United States Patent
Kouzu et al.

(10) Patent No.: US 6,190,648 B1
(45) Date of Patent: Feb. 20, 2001

(54) HAIR COSMETICS

(75) Inventors: Emiko Kouzu; Takashi Itou; Atsushi Uzu; Tadashi Nomura; Michiko Asami; Aya Hirano; Yoshiaki Itou, all of Tokyo (JP)

(73) Assignee: Kao Corporation, Tokyo (JP)

( * ) Notice: Under 35 U.S.C. 154(b), the term of this patent shall be extended for 0 days.

(21) Appl. No.: 09/100,248

(22) Filed: Jun. 19, 1998

(30) Foreign Application Priority Data

Jun. 25, 1997 (JP) .................................................... 9-169322
Dec. 5, 1997 (JP) .................................................... 9-335255

(51) Int. Cl.[7] ................ A61K 7/13; A61K 7/06
(52) U.S. Cl. ................ 424/70.6; 424/70.11; 424/70.16; 514/951
(58) Field of Search ............................. 424/70.11, 70.16, 424/70.6

(56) References Cited

U.S. PATENT DOCUMENTS 3,926,659 * 12/1975 Bernhard et al. ..................... 106/418
4,038,099 * 7/1977 DeLuca, Jr. et al. .
5,116,664 * 5/1992 Kimura et al. .
5,798,109 * 8/1998 Yanagida et al. ..................... 424/401

OTHER PUBLICATIONS

Hawley, Gessner G. The Condensed Chemical Dictionary. New York: Van Nostrand Reinhold Company. 1981, 10th Ed., p. 904.*

* cited by examiner

Primary Examiner—Diana Dudash
Assistant Examiner—Alysia Berman
(74) Attorney, Agent, or Firm—Oblon, Spivak, McClelland, Maier & Neustadt, P.C.

(57) ABSTRACT

In a hair cosmetic containing titanium-dioxide-coated mica, titanium-dioxide-coated mica with particle diameters of 20 μm or larger is used in a proportion not more than 10% by volume in the total volume of the titanium-dioxide-coated mica so that, when applied to hair, it may not impart an unnaturally glittering impression to the hair. To improve re-dispersibility of such a hair cosmetic, a carboxyvinyl polymer and an amphoteric macromolecule may be used in combination.

6 Claims, No Drawings

HAIR COSMETICS

BACKGROUND OF THE INVENTION

1. Field of the Invention

This invention relates to a hair cosmetic that can impart a temporary change in the color tone of hair. More particularly, it relates to a hair cosmetic that contains titanium-dioxide-coated mica but can change the color tone of hair into a color tone with a natural impression.

2. Description of the Related Art

As hair cosmetics for imparting changes in the color tone of hair, permanent hair dyes (hair colors, bleach and colors), hair bleaches (bleaches), semi-permanent hair dyes (hair manicures) and temporary hair dyes are conventionally used from the viewpoint of retention of color tones changed.

Of these, the use of permanent hair dyes, semi-permanent hair dyes or hair bleaches tends to cause problems such as hair damage and skin dyeing. Moreover, there are problems that these can be handled with difficulty for users who want to treat their own hair by themselves and also that, if color tones have been changed into tones not originally intended, it is actually impossible to readily restore the original color.

On the other hand, the use of temporary hair dyes ay cause neither hair damage nor skin dyeing. Moreover, they have an advantage that the original color tone can be restored by shampooing the colored hair to easily wash off the temporary hair dye adhering to the hair.

Recently, as a kind of such temporary hair dyes, a hair cosmetic mixed with titanium-dioxide-coated mica is proposed (see Japanese Patent Applications Laid-open No. 58-124713, No. 62-4219 and No. 1-121208), which mica has been used from old times as a pearlescent pigment in cosmetics and hair-treating materials and has a good hiding power. When hair cosmetics containing such titanium-dioxide-coated mica are used in hair, the hair can be colored and then the hair colored can be readily restored to the original color tone of hair by shampooing.

As a different kind of such temporary hair dyes, a hair color foam aerosol is proposed which is obtained by filling an aerosol pressure container with a) a base solution obtained by mixing, in a mixed solvent of ethanol and water, such titanium-dioxide-coated mica, a carboxyvinyl polymer used as a thickening agent capable of highly effectively preventing the titanium-dioxide-coated mica from settling and an anionic resin used as a binder for fixing the titanium-dioxide-coated mica onto the hair, and b) an aerosol propellant added to the base solution (Japanese Patent Application Laid-open No. 62-255414).

However, conventional hair cosmetics containing the titanium-dioxide-coated mica have had a problem of a difficulty in their daily use because they not only color the hair but also impart a glittering, strongly pearly impression to the hair.

In particular, the hair color foam aerosol disclosed in Japanese Patent Application Laid-open No. 62-255414, has problems that the titanium-dioxide-coated mica, though having a good re-dispersibility in the base solution, tends to agglomerate on the hair to cause flaking and also that the color formation attributable to the titanium-dioxide-coated mica is too insufficient to well change the color of hair. Moreover, it may undesirably impart a glittering impression with an unnaturally strongly pearly appearance.

SUMMARY OF THE INVENTION

The present invention was made in order to solve the above problems the prior art has had. Accordingly, a first object of the present invention is to make it possible to color hair in a natural impression when hair cosmetics containing titanium-dioxide-coated mica are applied to the hair. Also, a second object of the present invention is to make it possible to realize a good dispersibility for such hair cosmetics.

The present inventors took note of the fact that the relationship between particle diameter of titanium-dioxide-coated mica and the glittering impression imparted to hair has not been taken into consideration at all in the conventional hair cosmetics containing the titanium-dioxide-coated mica, and have reached a finding that the color tone of hair can be changed into a natural tone without imparting the glittering impression to hair, when titanium-dioxide-coated mica with a relatively large particle diameter is held in a smaller proportion in the total volume of titanium-dioxide-coated mica used. On the basis of such a finding, they have accomplished a hair cosmetic according to a first embodiment of the present invention that can achieve the first object.

More specifically, as the first embodiment, the present invention provides a hair cosmetic containing titanium-dioxide-coated mica, wherein titanium-dioxide-coated mica with particle diameters of 20 $\mu$m or larger is in a proportion not more than 10% by volume in the total volume of the titanium-dioxide-coated mica.

The present inventors also made extensive studies in order to achieve the above second object. As a result, they have reached, in addition to the above finding, the following findings (i) and (ii):

(i) that, when titanium-dioxide-coated mica with a relatively small particle diameter is mixed in hair cosmetics, the hair cosmetics tend to agglomerate, have an insufficient re-dispersibility, tend to cause caking and may insufficiently form colors on the hair; and (ii) that, even if titanium-dioxide-coated mica with a relatively small particle diameter is used, the titanium-dioxide-coated mica can be well re-dispersed when a carboxyvinyl polymer and an amphoteric macromolecule are used in combination in a specified proportion, and the color tone of hair can be changed into a natural tone without imparting any glittering impression to the hair. On the basis of such findings, they have accomplished a hair cosmetic according to a second embodiment of the present invention.

More specifically, as the second embodiment, the present invention provides a hair cosmetic in which, in addition to the titanium-dioxide-coated mica with particle diameters of 20 $\mu$m or larger contained in a proportion not more than 10% by volume, a carboxyvinyl polymer and an amphoteric macromolecule are used in combination.

DETAILED DESCRIPTION OF THE INVENTION

The hair cosmetic according to the first embodiment of the present invention contains titanium-dioxide-coated mica. The reason why the titanium-dioxide-coated mica is used is as follows:

The titanium-dioxide-coated mica commonly refers to those comprising a laminar natural mica (white mica, black mica or gold mica) of from about several $\mu$m to about hundreds of $\mu$m in maximum size and from about 0.05 to about 1 $\mu$m in thickness or a synthetic mica of from about 0.1 $\mu$m to about 50 $\mu$m in maximum size and from about 0.05 to about 50 $\mu$m in thickness, the laminar surfaces of which are coated with titanium dioxide to have titanium dioxide layers. Such titanium-dioxide-coated mica itself has a white appearance, and forms an interference color of yellow, red, blue or green depending on the thickness of titanium dioxide layers. Thus, the mixing of the titanium-dioxide-coated mica in hair cosmetics, when the hair cosmetics are applied to black hair, brings about very vivid color formation by contrast with black background of the hair to which the titanium-dioxide-coated mica has adhered.

Incidentally, the particle diameter referred to on the titanium-dioxide-coated mica is expressed variously by maximum size measured with a microscope or average value determined by a light-scattering method. The particle diameter of titanium-dioxide-coated mica in the present invention is meant by a value obtained by the Coulter method. According to the Coulter method, particle size distribution can be measured easily using, e.g., Coulter Multicizer 020487 (manufactured by Coulter Electronics Co; with an aperture of 100 $\mu$m diameter). To make calibration, a monodisperse silica latex may be used. In this measurement, in order to make measurement without causing the aggregation of titanium-dioxide-coated mica particles, the measurement must be made after the particles is diluted with a surface-active agent solution (e.g., an aqueous 0.03% polyoxyethylene alkyl ether solution) followed by ultrasonic treatment.

Commonly available titanium-dioxide-coated mica has a broad particle size distribution, ranging from very fine particle diameters of from 1 to 2 $\mu$m to relatively large particle diameters of 20 $\mu$m or larger. According to findings made by the present inventors, those which strongly impart a glittering pearly impression to hair are particles with the relatively large particle diameters of 20 $\mu$m or larger, and also those in which titanium-dioxide-coated mica with particle diameters of 20 $\mu$m or larger is in a proportion more than 10% by volume in the total volume of the titanium-dioxide-coated mica.

Accordingly, in the hair cosmetic according to the first embodiment of the present invention, the proportion of the titanium-dioxide-coated mica with particle diameters of 20 $\mu$m or larger is controlled to be not more than 10% by volume, preferably not more than 7% by volume, more preferably not more than 5% by volume, and still more preferably not more than 1% by volume, in the total volume of the titanium-dioxide-coated mica contained therein. Hence, when the hair cosmetic according to the first embodiment of the present invention is applied to hair, the color tone of hair can be changed into a natural tone without imparting the glittering pearly impression to the hair.

Titanium dioxide used in the titanium-dioxide-coated mica is structurally grouped into the rutile type and the anatase type. The rutile type titanium dioxide, having a higher refractive index and superior reflecting properties, is preferred because it can provide a greater change in color and a vivid hair color.

The rutile type titanium dioxide may be coated on mica by a known method including a method in which tin oxide is used (U.S. Pat. Nos. 4,038,099 and 4,086,100) and a method in which iron and at least one of calcium oxide, magnesium oxide and zinc oxide are used (Japanese Patent Application Laid-open No. 7-316464). From the viewpoint of safety, the latter method is preferred.

Titanium-dioxide-coated mica produced by the latter method consequently contains iron and at least one of calcium oxide, magnesium oxide and zinc oxide. Here, if the iron is in a too small content in the titanium-dioxide-coated mica, the titanium-dioxide-coated mica may have an insufficient interference color. If it is in a too large content, the titanium-dioxide-coated mica may turn pale brown to make color changes lack in beauty when applied to the hair. Hence, the iron may preferably be in a content of from 0.125 to 1% by weight based on the weight of mica particles to be coated with the titanium dioxide. Also, if at least one of calcium oxide, magnesium oxide and zinc oxide is in a too small content in the titanium-dioxide-coated mica, the rutile type titanium dioxide may not be well formed to make color changes and gloss poor when applied to the hair. Hence, it may preferably be in a content of at least 0.05% by weight based on the weight of mica particles to be coated with the titanium dioxide.

As the titanium-dioxide-coated mica used in the hair cosmetic according to the first embodiment of the present invention, various titanium-dioxide-coated mica may be used which satisfies the condition that particles with particle diameters of 20 $\mu$m or larger are in a proportion not more than 10% by volume. For example, titanium-dioxide-coated mica coated with titanium dioxide alone, and colored titanium-dioxide-coated mica such as titanium-dioxide-coated mica coated with red iron oxide, titanium-dioxide-coated mica coated with zinc white, titanium-dioxide-coated mica coated with Iron Blue, titanium-dioxide-coated mica coated with Carmine, titanium-dioxide-coated mica coated with black iron oxide, titanium-dioxide-coated mica coated with Red No.226, and titanium-dioxide-coated mica coated with barium sulfate, as well as colored titanium-dioxide-coated mica having a low-grade titanium oxide layer as disclosed in Japanese Patent Application Laid-open No. 5-43417.

The titanium-dioxide-coated mica used in the present invention can be readily obtained by sieving commercially available titanium-dioxide-coated mica containing particles with diameters of 20 $\mu$m or larger in a proportion more than 10% by volume, to remove the portion of larger particles. Among the commercially available titanium-dioxide-coated mica, those which fulfill the condition of the present invention need not be sieved, and such commercially available products may be used as they are.

As a specific example of the titanium-dioxide-coated mica, it may include FLAMENCO SATIN GOLD (trade name; the proportion of particles with diameters of 20 $\mu$m or larger is 0.1% by volume), available from Mearl Co.

As the titanium-dioxide-coated mica, those having been treated to make particle surfaces hydrophobic in order to improve its stability or dispersibility in the hair cosmetic may be used, having been treated with, e.g., silicone oil, an aliphatic metal salt, alkyl phosphate, an alkali metal salt or amine salt of alkyl phosphate, an N-mono, long-chain (C8–C22) aromatic acyl basic amino acid, or a fluorine compound having a perfluoroalkyl group.

In the hair cosmetic according to the first embodiment of the present invention, the titanium-dioxide-coated mica may preferably be in a content of from 0.5 to 20% by weight, more preferably from 1 to 15% by weight, and still more preferably from 2 to 10% by weight, because if it is in a too small content the color of hair may be less changed and if it is in a too large content the hair may undesirably have a stiff feel.

In order to stably fix the titanium-dioxide-coated mica to the hair, the hair cosmetic according to the first embodiment of the present invention may preferably be mixed with a pigment-fixing resin. The pigment-fixing resin also functions as a hair-setting resin, and hence the hair cosmetic mixed with the pigment-fixing resin can have the effect of hair dressing.

The pigment-fixing resin may include various polymers of synthetic or natural types, amphoteric polymers, anionic polymers, cationic polymers and nonionic polymers, any of which may be used.

Here, the amphoteric polymers may include Methacryloyl ethyl betain/Acrylates copolymers, as exemplified by YUKAFORMER AM-75, YUKAFORMER SM, YUKAFORMER 202 (trade names; all available from Mitsubishi Chemical Industries Limited); and hydroxypropyl acrylate/butylaminoethyl methacrylate/acrylic acid octylamide copolymers as exemplified by AMPHOMER 28-4910 and LV-71 (trade names; all available from National Starch Co.). In particular, YUKAFORMER AM-75 or YUKAFORMER 202 may preferably be used.

The anionic polymers may include, e.g., various polymers containing carboxyl groups. In particular, acrylic or methacrylic acid/acrylic or methacrylic acid copolymers or salts thereof may preferably be used.

The cationic polymers may preferably include vinyl pyrrolidone/quaternized dimethylaminoethyl methacrylate copolymers as exemplified by GUFQUAT 734, GUFQUAT 755N (trade names; all available from ISP Corp.) and PQ-11 (trade name; available from BASF Corp.).

The nonionic polymers may include polyvinyl pyrrolidone/vinyl acetate copolymers as exemplified by Luviskol VA 28E, 37E, 55E, 64E, 73E (trade name; all available from BASF Corp.), and PVP/VA E-735, E-635, E-535, E-335, S-630, W-735 (trade name; all available from ISP Corp.).

As natural macromolecules or derivatives thereof, they may preferably include, e.g., cationized cellulose and hydroxypropyl chitosan.

Of these pigment-fixing resins, with regard to those having acidic groups, those in which part or the whole of their acidic groups has been neutralized and converted into salts are preferred in view of feel or the like.

Of the pigment-fixing resins, with regard to those having basic groups, those in which part or the whole of their basic groups has been neutralized and converted into salts are preferred.

Any of these pigment-fixing resins may be mixed in an amount of from 1 to 100 parts by weight, preferably from 10 to 100 parts by weight, and more preferably from 20 to 50 parts by weight, based on 100 parts by weight of the titanium-dioxide-coated mica.

The hair cosmetic according to the first embodiment of the present invention may optionally and appropriately be further mixed with an anionic surface-active agent such as sodium stearate, sodium lauryl stearate or sodium polyoxyethylene alkyl ether sulfates; a cationic surface-active agent such as stearyl trimethylammonium chloride; a nonionic surface-active agent such as polyoxyethylene alkyl ethers, glycerol fatty acid esters, polyoxyethylene hardened castor oil, polyoxyethylene fatty acid esters, polyoxyethylene sorbitol fatty acid esters or coconut oil fatty acid diethanolamides; an amphoteric surface-active agent such as lauryl betaine; a hydrocarbon such as squalane or liquid paraffin; a silicone oil such as dimethylpolysiloxane, methylphenylpolysiloxane or amino-modified silicone; a polyol such as glycerol or propylene glycol; a carboxy vinyl polymer (e.g., CARBOPOL 940, trade name, available from B.F. Goodrich); a thickening agent such as xanthane gum; a dispersion stabilizer such as clay mineral; and an oil agent such as higher alcohols, higher fatty acid esters and animal or vegetable oils; as well as a humectant, a neutralizing agent, an anticeptic, an ultraviolet light absorbent, an antioxidant, vitamin, extract, and a perfume.

Here, the titanium-dioxide-coated mica used in the hair cosmetic according to the first embodiment of the present invention may be used in combination with a carboxyvinyl polymer and also an amphoteric macromolecule may be used in combination, to obtain a hair cosmetic according to the second embodiment of the present invention, which has a superior re-dispersibility in addition to the advantages the hair cosmetic according to the first embodiment of the present invention has.

The titanium-dioxide-coated mica in the hair cosmetic according to the second embodiment of the present invention may preferably be in a content relatively smaller than the hair cosmetic according to the first embodiment. If, however, it is in a too small content, the color of hair may be less changed and, if it is in a too large content, the hair may undesirably have a stiff feel. Thus, the titanium-dioxide-coated mica may preferably be in a content of from 0.5 to 10% by weight, more preferably from 1 to 7% by weight, and still more preferably from 2 to 5% by weight.

As mentioned above, the hair cosmetic according to the second embodiment of the present invention makes use of a carboxyvinyl polymer. Hence, the titanium-dioxide-coated mica, commonly having a relatively great specific gravity among the components of hair cosmetics, can be prevented from settling or caking.

The carboxyvinyl polymer may include, e.g., CARBOPOL 980 and CARBOPOL 981 (trade names; all available from B.F. Goodrich).

The carboxyvinyl polymer may preferably be mixed in the hair cosmetic in an amount of from 0.01 to 0.2% by weight, and more preferably from 0.03 to 0.1% by weight, because if it is in a too small quantity the titanium-dioxide-coated mica may have an insufficient re-dispersibility and if it is in a too large quantity the hair cosmetic may have a sticky feel.

The hair cosmetic according to the second embodiment of the present invention also contains an amphoteric macromolecule. Hence, the titanium-dioxide-coated mica can be prevented from undergoing the aggregation on hair that may occur when other resins such as anionic resin are used, and the titanium-dioxide-coated mica can be fixed to hair without causing any lowering of color-forming properties of the titanium-dioxide-coated mica.

Here, As the amphoteric macromolecule, polymers represented by the following formula (1), having a molecular weight of from 40,000 to 300,000, are particularly preferably usable.

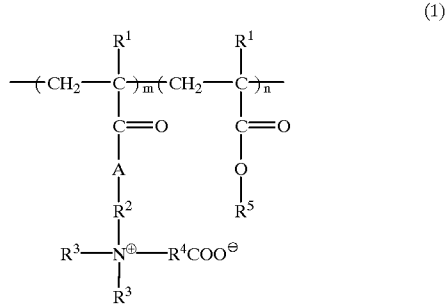

(1)

wherein $R^1$ and $R^3$ each independently represent a hydrogen atom or a methyl group; $R^2$ and $R^4$ each represent a an alkylene group having 1 to 4 carbon atoms (e.g., a methylene group, an ethylene group and a propylene group); $R^5$ represents a saturated or unsaturated hydrocarbon group having 1 to 24 carbon atoms (e.g., an ethyl group, a butyl group, an octyl group, a lauryl group and a stearyl group); A is not present or represents an oxygen atom or an NH group; and m and n are each an integer that satisfies m:n=20:80 to 90:10.

The amphoteric macromolecule may preferably be mixed in the hair cosmetic in an amount of from 0.2 to 3% by weight, and more preferably from 0.5 to 1% by weight, because if it is in a too small quantity the titanium-dioxide-coated mica can not be well fixed to hair and if it is in a too large quantity the hair may have a stiff feel.

For the purpose of improving the dispersibility of the titanium-dioxide-coated mica, the hair cosmetic according to the second embodiment of the present invention may preferably be further incorporated with any one or both of a nonionic surfactant and an anionic surfactant.

Such a nonionic surfactant may include polyoxyethylene alkyl ethers, glycerol fatty acid esters, polyoxyethylene hydrogenated castor oils, polyoxyethylene fatty acid esters and coconut fatty acid diethanol amides. The anionic surfactant may include polyoxyethylene alkyl ether phosphates, polyoxyethylene alkyl ether sulfates, alkyl sulfates and fatty acid salts.

The nonionic surfactant and the anionic surfactant may preferably be mixed in the hair cosmetic in an amount of from 0.1 to 3% by weight, and more preferably from 0.3 to 1% by weight, in total because if they are in a too small quantity they may less contribute to the dispersibility of the titanium-dioxide-coated mica and if they are in a too large quantity the hair may have a sticky feel.

In order to make also the amphoteric macromolecule contribute to the stable fixing of the titanium-dioxide-coated mica to hair, the hair cosmetic according to the second embodiment of the present invention may additionally contain the pigment-fixing resin as described in the hair cosmetic according to the first embodiment. The pigment-fixing resin also functions as a hair-setting resin, and hence the hair cosmetic mixed with the pigment-fixing resin can have the effect of hair dressing. Such a pigment-fixing resin may include acrylic resins and polyvinyl pyrrolidone/vinyl acetate copolymers.

Such a pigment-fixing resin may preferably be mixed in an amount of 1 to 1,000 parts by weight, more preferably from 10 to 100 parts by weight, and still more preferably from 20 to 50 parts by weight, based on 100 parts by weight of the titanium-dioxide-coated mica.

The hair cosmetic according to the second embodiment of the present invention may optionally and appropriately be further mixed with a cationic surface-active agent such as stearyl trimethyl ammonium chloride, an amphoteric surface-active agent such as lauryl betaine, a hydrocarbon such as squalane or liquid paraffin; a silicone oil such as dimethylpolysiloxane, methylphenylpolysiloxane or amino-modified silicone, a polyol such as glycerol or propylene glycol, a thickening agent such as xanthane gum, a dispersion stabilizer such as clay mineral, and an oil agent such as higher alcohols, higher fatty acid esters or animal or vegetable oils; as well as a humectant, a neutralizing agent, an anticeptic, an ultraviolet light absorbent, an antioxidant, vitamin, extract, and a perfume.

The hair cosmetics according to the first and second embodiments of the present invention may further be mixed with dyes including tar dyes and natural dyes generally used in cosmetics. Also, for the purpose of being dressed up differently than usual, a pearling agent such as large-diameter titanium-dioxide-coated mica, white mica or synthetic mica may appropriately be mixed.

In addition to the foregoing essential components and optional components, the hair cosmetics according to the first and second embodiments of the present invention may also preferably be incorporated with water or ethanol or both of these as a dispersion medium.

The above hair cosmetics according to the first and second embodiments of the present invention are desired to be formed into aerosol cosmetics when their form of use is taken into account. In such an instance, the hair cosmetic may preferably be incorporated with an aerosol propellant in addition to the titanium-dioxide-coated mica. Such an aerosol propellant may include liquefied petroleum gas (LPG), dimethyl ether, carbon dioxide, compressed nitrogen and compressed air. Any of these may be used in combination of two or more.

The aerosol propellant may preferably be used in an amount of from 5 to 50% by weight, and more preferably from 7 to 20% by weight, based on the weight of the base solution containing the titanium-dioxide-coated mica in the case of petroleum gas or dimethyl ether.

Forms of preparations suited for the first and second embodiments of the present invention may include gels, sprays, creams, lotions, foams, waxes, spray foams and post-foaming gels. In particular, foams are preferred.

EXAMPLES

The present invention will be described below in greater detail by giving Experiments.

As titanium-dioxide-coated mica used in the following Experiments, titanium-dioxide-coated micas A to F were used, each having average particle diameter and proportion (% by volume) of titanium-dioxide-coated mica with particle diameters of 20 $\mu$m or larger as shown in Table 1.

As titanium-dioxide-coated mica A, FLAMENCO SATIN GOLD 260M (trade name; rutile type, available from Mearl Co.) was used as it was. As titanium-dioxide-coated mica F, TIMIRON SUPER GOLD (trade name; anatase type, available from Merck & Co., Inc.) was used as it was. As titanium-dioxide-coated micas B to E, those obtained by classifying the titanium-dioxide-coated mica F by means of an MDS classifier manufactured by Nippon Pneumatic Industries Co. were used.

TABLE 1

| (i)* Mica | (ii)* Diameter ($\mu$m) | (iii)* Proportion (% by volume) |
| --- | --- | --- |
| A | 5.2 | 0.1 |
| B | 7.4 | 1.0 |
| C | 6.9 | 3.7 |
| D | 8.7 | 7.3 |
| E | 12.0 | 10.9 |
| F | 13.0 | 14.0 |

Notes of Table 1:
(i)* Kind of Titanium Dioxide Coated Mica)
(ii)* Average Particle Diameter
(iii)* Proportion of titanium-dioxide-coated mica with particle diameters of 20 $\mu$m or larger Experiments 1 to 7

Components except LPG, as shown in Table 2, were mixed by a conventional method, and the mixture obtained was injected into a commercially available aerosol foam container, which was further filled with the LPG (0.4 MPa). Thus, hair cosmetics were obtained in the form that they were filled in aerosol foam containers.

Evaluation

The hair cosmetic prepared in each Experiment and filled in the aerosol foam container was applied to hair, where the change in the color of hair (hereinafter often "hair-color change") was tested and evaluated in the following way.

Hair-color Change Test

The aerosol foam of the hair cosmetic was spouted out of the aerosol foam container, and an about 1 g portion thereof was coated on a hair sample of 15 cm long (about 5 g). The hair sample thus treated was combed to make it fitting, followed by drying. After the drying, ten (10) specialist panelists visually observed changes in the color of hair and their naturalness (degree of glittering impression) to express them as marks according to the following evaluation criteria. Average marks of the ten specialist panelists were ranked according to the following evaluation criteria.

Results obtained are shown in Table 2. The result of ranking is desired to be A or B in practical use.

Hair-color change:

| | |
|---|---|
| A great change is seen: | 2 points |
| A little change is seen: | 1 point |
| Little change is seen: | 0 point |

Naturalness:

| | |
|---|---|
| Glittering impression is little seen: | 2 points |
| Glittering impression is a little seen with a little unnaturalness: | 1 point |
| Glittering impression is greatly seen with unnaturalness: | 0 point |

Evaluation criteria:

| Rank | Average mark |
|---|---|
| A: | From 1.5 to 2. |
| B: | From 1 to less than 1.5. |
| C: | From 0.5 to less than 1. |
| D: | Less than 0.5. |

TABLE 2

| | (% by weight) | | | | | | |
|---|---|---|---|---|---|---|---|
| | Experiment | | | | | | |
| Components | 1 | 2 | 3 | 4 | 5 | 6 | 7 |
| Titanium-dioxide-coated mica: | | | | | | | |
| A | 3.0 | 0.5 | — | — | — | — | — |
| B | — | — | 3.0 | — | — | — | — |
| C | — | — | — | 3.0 | — | — | — |
| D | — | — | — | — | 3.0 | — | — |
| E | — | — | — | — | — | 3.0 | — |
| F | — | — | — | — | — | — | 3.0 |
| Anionic polymer*[1] | 2.0 | 2.0 | 2.0 | 2.0 | 2.0 | 2.0 | 2.0 |
| Surface-active agent*[2] | 1.0 | 1.0 | 1.0 | 1.0 | 1.0 | 1.0 | 1.0 |
| Ethanol | 5.0 | 5.0 | 5.0 | 5.0 | 5.0 | 5.0 | 5.0 |
| Water | bal. | bal. | bal. | bal. | bal. | bal. | bal. |
| LPG (0.4 MPa) | 10.0 | 10.0 | 10.0 | 10.0 | 10.0 | 10.0 | 10.0 |
| - Evaluation - | | | | | | | |
| Hair-color change: | A | B | A | B | B | C | C |
| Naturalness: | A | A | A | A | B | D | D |

Notes of Table 2:
*[1]PLASCIZE L-75CB (act. 50%), available from Goo Chemical Co., Ltd.
*[2]Polyoxyethylene (9) sec-tetradecyl ether.

As can be seen from Table 2, the hair cosmetics of Experiments 1 to 5 according to the present invention was able to change the color tone of hair in a natural feeling.

On the other hand, the hair cosmetics of Experiments 6 and 7 was not able to change the color tone of hair especially in a natural feeling because the titanium-dioxide-coated mica with particle diameters of 20 μm or larger was in a proportion more than 10% by volume in the total volume of the titanium-dioxide-coated mica used.

Experiment 8

Components except LPG, as shown in Table 3, were mixed by a conventional method, and the mixture obtained was injected into a commercially available hair spray container, which was further filled with the LPG (0.25 MPa). Thus, a hair cosmetic was obtained in the form that it was filled in a hair spray container. On the hair cosmetic thus obtained, the hair-color change and naturalness were evaluated in the same manner as in Experiment 1.

Results obtained are shown in Table 3. As can be seen from Table 3, the hair cosmetic of Experiment 8 was able to change the color tone of hair in a natural feeling.

TABLE 3

| Components | (% by weight) |
|---|---|
| Titanium-dioxide-coated mica A | 2.0 |
| Amphoteric polymer (AMPHOMER 28-4910, available from National Starch Co.) | 1.0 |
| 2-Amino-2-methylpropanol | 0.17 |
| Squalane | 0.1 |
| Methyl phenyl polysiloxane (KF-53, available from Shin-Etsu Chemical Co., Ltd.) | 0.2 |
| Perfume | 0.1 |
| Ethanol | balance |
| LPG (0.25 MPa) | 40.0 |
| - Evaluation - | |
| Hair-color change: | A |
| Naturalness: | A |

Experiment 9

Components except LPG, as shown in Table 4, were mixed by a conventional method, and the mixture obtained was injected into a commercially available aerosol foam container, which was further filled with the LPG (0.4 MPa). On the aerosol foam of the hair cosmetic thus obtained, the hair-color change and naturalness were evaluated in the same manner as in Experiment 1.

Results obtained are shown in Table 4. As can be seen from Table 4, the hair cosmetic of Experiment 9 was able to change the color tone of hair in a natural feeling.

TABLE 4

| Components | (% by weight) |
|---|---|
| Titanium-dioxide-coated mica A | 3.0 |
| Amphoteric polymer (YUKAFORMER 202(act.30%), available from Mitsubishi Chemical Industries Limited) | 2.0 |
| Stearyl trimethylammonium chloride | 0.3 |
| Polyoxyethylene (9EO) tetradecyl ether | 0.5 |
| Squalane | 0.5 |
| Methylparaben | 0.1 |
| Ethanol | 5.0 |
| Water | balance |
| Perfume | 0.2 |
| LPG (0.4 MPa) | 10.0 |
| - Evaluation - | |
| Hair-color change: | A |
| Naturalness: | A |

Experiment 10

Components as shown in Table 5 were mixed by a conventional method to obtain a gel type hair cosmetic. On the hair cosmetic thus obtained, the hair-color change and naturalness were evaluated in the same manner as in Experiment 1.

Results obtained are shown in Table 5. As can be seen from Table 5, the gel type hair cosmetic of Experiment 10 was able to change the color tone of hair in a natural feeling.

TABLE 5

| Components | (% by weight) |
|---|---|
| Titanium-dioxide-coated mica*3 | 10.0 |
| Xanthane gum*4 | 1.0 |
| Anionic polymer*1 | 2.0 |
| Polyoxyethylene hydrogenated castor oil (40EO) | 0.5 |
| Glycerol | 0.1 |
| Ethanol | 20.0 |
| Perfume | 0.15 |
| Purified water | balance |
| - Evaluation - | |
| Hair-color change: | B |
| Naturalness: | A |

Notes of Table 5:
*3: Average particle diameter: 5.2 μm; proportion of particles with diameters of 20 μm or larger: 0.1% by volume; FLAMENCO SATIN BLUE 660M (rutile type, available from Mearl Co.).
*4: ECHO GUM T, available from Dainippon Pharmaceutical Co., Ltd.).

Experiment 11

Components as shown in Table 6 were mixed by a conventional method to obtain a foam type hair cosmetic. On the hair cosmetic thus obtained, the hair-color change and naturalness were evaluated in the same manner as in Experiment 1.

Results obtained are shown in Table 6. As can be seen from Table 6, the foam type hair cosmetic of Experiment 11 was able to change the color tone of hair in a natural feeling.

TABLE 6

| Components | (% by weight) |
|---|---|
| Titanium-dioxide-coated mica*5 | 1.0 |
| Amphoteric polymer | 1.5 |
| (YUKAFORMER 202(act.30%), available from Mitsubishi Chemical Industries Limited) | |
| Liquid Petrolatum | 0.1 |
| Dimethyl polysiloxane (5000 cs) | 0.1 |
| Stearyl trimethylammonium chloride | 0.2 |
| Polyoxyethylene (9EO) sec-tetradecyl ether | 0.4 |
| Ethanol | 8.0 |
| Birch Extract | 0.1 |
| (available from Ichimaru Pharcos Co., Ltd.) | |
| Purified water | balance |
| LPG (0.45 MPa) | 8.5 |
| - Evaluation - | |
| Hair-color change: | B |
| Naturalness: | A |

Notes of Table 6:
*5: Average particle diameter: 7.4 μm; proportion of particles with diameters of 20 μm or larger: 0.8% by volume [titanium-dioxide-coated mica obtained by classifying FLAMENCO ORANGE 320 (anatase type, available from Mearl Co.) having an average particle diameter: 12.1 μm and a proportion of particles with diameters of 20 μm or larger: 12.8% by volume].

Experiment 12

Components except LPG and dimethyl ether, as shown in Table 7, were mixed by a conventional method, and the mixture obtained was injected into a commercially available aerosol foam container, which was further filled with the LPG (0.6 MPa) and dimethyl ether. Thus, a foam type hair cosmetic was obtained. On the foam type hair cosmetic thus obtained, the hair-color change and naturalness were evaluated in the same manner as in Experiment 1.

Results obtained are shown in Table 7. As can be seen from Table 7, the foam type hair cosmetic of Experiment 12 was able to change the color tone of hair in a natural feeling.

TABLE 7

| Components | (% by weight) |
|---|---|
| Titanium-dioxide-coated mica*6 | 4.0 |
| Amphoteric polymer | 3.0 |
| (YUKAFORMER SM(act.30%), available from Mitsubishi Chemical Industries Limited) | |
| Isopropyl myristate | 0.1 |
| Isostearyl glyceryl ether | 0.2 |
| Polyoxyethylene (9EO) sec-tetradecyl ether | 0.5 |
| Red No. 404 | 2.0 |
| Methylparaben | 0.1 |
| Cycloprotein extract solution | 0.05 |
| (SILKGEN G SOLUBLE KE, available from Ichimaru Pharcos Co., Ltd.) | |
| Ethanol | 5.0 |
| Water | balance |
| Perfume | 0.2 |
| LPG (0.6 MPa) | 8.0 |
| Dimethyl ether | 2.0 |
| - Evaluation - | |
| Hair-color change: | A |
| Naturalness: | A |

Notes of Table 7:
*6: Average particle diameter: 5.4 μm; proportion of particles with diameters of 20 μm or larger: 0.1% by volume; FLAMENCO SATIN ORANGE 360M (rutile type, available from Mearl Co.).

Experiment 13

Components as shown in Table 8 were mixed by a conventional method to obtain a gel type hair cosmetic. On the hair cosmetic thus obtained, the hair-color change and naturalness were evaluated in the same manner as in Experiment 1.

Results obtained are shown in Table 8. As can be seen from Table 8, the gel type hair cosmetic of Experiment 13 was able to change the color tone of hair in a natural feeling.

TABLE 8

| Components | (% by weight) |
|---|---|
| Titanium-dioxide-coated mica A | 20.0 |
| Liquid isoparaffin | 10.0 |
| Polyoxyethylene (3EO) oleyl ether phosphate | 5.5 |
| Polyoxyethylene (5EO) cetyl ether | 7.0 |
| Polyoxyethylene (20EO) cetostearyl ether | 2.4 |
| Glycerol | 3.0 |
| 1,3-butanediol | 4.0 |
| Sorbitol | 10.0 |
| Amino-modified silicone emulsion | 0.5 |
| (SM-8702C, available from Toray Dow Corning Corp.) | |
| Potassium hydroxide | 1.6 |
| Perfume | 0.2 |
| Purified water | balance |
| - Evaluation - | |
| Hair-color change: | B |
| Naturalness: | A |

Experiment 14

Components except LPG, as shown in Table 9, were mixed by a conventional method, and the mixture obtained was injected into a container with a comb-type attachment, which was further filled with the LPG (0.4 MPa). On the foam type hair cosmetic thus obtained, the hair-color change and naturalness were evaluated in the same manner as in Experiment 1.

Results obtained are shown in Table 9. As can be seen from Table 9, the foam type hair cosmetic of Experiment 14 was able to change the color tone of hair in a natural feeling.

TABLE 9

| Components | (% by weight) |
|---|---|
| Mixed titanium-dioxide-coated mica*7 | 3.5 |
| (Titanium-dioxide-coated mica*8 | 2.0) |
| (Titanium-dioxide-coated mica*9 | 1.5) |
| Amphoteric polymer | 1.5 |
| (YUKAFORMER 202(act.30%), available from | |
| Mitsubishi Chemical Industries Limited) | |
| Cyclic silicone | 0.2 |
| Olive oil | 0.1 |
| Dialkyl(C12—C16)dimethylammonium chloride | 0.1 |
| Polyoxyethylene (9EO) sec-tetradecyl ether | 0.5 |
| Ethanol | 5.0 |
| Perfume | 0.05 |
| Purified water | balance |
| LPG (4.0 kg/m²) | 10.0 |
| - Evaluation - | |
| Hair-color change: | A |
| Naturalness: | B |

Notes of Table 9:
*7: A mixture of titanium-dioxide-coated mica*8 and titanium-dioxide-coated mica*9; average particle diameter of the mixture: 8.3 μm; proportion of particles with diameters of 20 μm or larger: 6.3% by volume.
*8: Average particle diameter: 5.2 μm; proportion of particles with diameters of 20 μm or larger: 0.1% by volume or less; FLAMENCO SATIN RED 460M (available from Mearl Co.).
*9: Average particle diameter: 12.5 μm; proportion of particles with diameters of 20 μm or larger: 14.6% by volume or less; FLAMENCO RED 420C (available from Mearl Co.).

Experiments 15 to 20

Components as shown in Table 10 were mixed by a conventional method, and the pH of the mixture was adjusted to 7.5. Forty five grams (45 g) of the mixture thus obtained and about 1 g of stainless steel balls were put into a commercially available aerosol can (container), which was further filled with 5 g of an aerosol propellant (liquefied petroleum gas; 0.4 MPa). Thus, aerosol (foam) type hair cosmetics were prepared.

Evaluation

Re-dispersibility of the hair cosmetic put in the aerosol container, prepared in each Experiment, was tested and evaluated in the following way. The hair cosmetic was also applied to hair, and the hair-color change was tested and evaluated in the same manner as in Experiment 1.

Re-dispersibility Test

Hair cosmetics containing well-dispersed titanium-dioxide-coated mica were left for 3 days. Thereafter, the aerosol containers were each shaken up and down and the number of times the container was shaken until the stainless steel balls began to move was counted, to make evaluation according to the following criteria. The up-and-down reciprocation was counted as one time.

Results obtained are shown in Table 10.

Re-dispersibility Evaluation Criteria:

| Rank | Criteria |
|---|---|
| A: | Not more than three times until the stainless steel balls begin to move. |
| B: | Four to ten times until the stainless steel balls begin to move. |
| C: | Eleven times or more until the stainless steel balls begin to move. |

TABLE 10

| | (% by weight) Experiment | | | | | |
|---|---|---|---|---|---|---|
| Components | 15 | 16 | 17 | 18 | 19 | 20 |
| Titanium-dioxide-coated mica: | | | | | | |
| A | 3.0 | 5.0 | 3.0 | — | 3.0 | — |
| D | — | — | — | 5.0 | — | — |
| F | — | — | — | — | — | 3.0 |
| Carboxyvinyl polymer*10 | 0.05 | 0.03 | 0.03 | 0.03 | 0.15 | 0.05 |
| Amphoteric macro-molecule*11 | 3.0 | 5.0 | 2.5 | 2.5 | 2.5 | 3.0 |
| Nonionic surfactant*12 | 0.5 | 0.5 | 0.5 | 0.5 | 0.5 | 0.5 |
| Anionic surfactant*13 | — | — | 0.3 | 0.3 | 0.3 | — |
| Sodium hydroxide | --in an amount for pH adjustment-- | | | | | |
| Disodium edetate | 0.1 | 0.1 | 0.1 | 0.1 | 0.1 | 0.1 |
| Ethanol | 15.0 | 10.0 | 15.0 | 15.0 | 15.0 | 15.0 |
| Purified water | bal. | bal. | bal. | bal. | bal. | bal. |
| Total: | 100 | 100 | 100 | 100 | 100 | 100 |
| - Evaluation - | | | | | | |
| Re-dispersibility: | A | A | A | A | A | A |
| Hair-color change: | A | A | A | B | A | C |

Noes of Table 10:
*10CARBOPOL 980, available from B. F. Goodrich.
*11YUKAFORMER 202 (act. 30%), available from Mitsubishi Chemical Industries Limited.
*12Polyoxyethylene tridecyl ether (SOFTANOL 90, trade name; available from Nippon Shokubai Kagaku Co., Ltd.
*13Polyoxyethylene (EO4) lauryl ether phosphate.

As shown in Table 10, the hair cosmetics of Experiments 15 to 19 had a good re-dispersibility, and was able to well change the color tone of hair. Moreover, they did not impart any unnaturally glittering impression to the hair.

However, the hair cosmetic of Experiment 20, making use of the titanium-dioxide-coated mica with particle diameters of 20 μm or larger in a proportion more than 10% by volume, was not able to well change the color tone, and was imparted a glittering impression with an unnatural feeling.

Experiment 21

Components as shown in Table 11 were mixed by a conventional method, and 45 g of the mixture thus obtained and about 1 g of stainless steel balls were put into a commercially available aerosol can (container), which was further filled with 5 g of an aerosol propellant (liquefied petroleum gas; 0.45 MPa). Thus, a hair cosmetic was obtained in the form that it was filled in a hair foam container. On the hair cosmetic thus obtained, the re-dispersibility and hair-color change were evaluated in the same manner as in Experiment 15.

Results obtained are shown in Table 11. As can be seen from Table 11, the hair cosmetic of Experiment 21 showed good results on both the re-dispersibility and the hair-color change. Moreover, it did not impart any unnaturally glittering impression to the hair.

TABLE 11

| Components | (% by weight) Experiment 21 |
|---|---|
| Titanium-dioxide-coated mica*14 | 3.0 |
| Carboxyvinyl polymer*10 | 0.03 |
| Amphoteric macromolecule*11 | 2.5 |
| Nonionic surfactant*12 | 0.5 |
| Anionic surfactant*13 | 0.3 |
| Polyether-modified silicone*15 | 0.4 |
| Squalane | 0.1 |
| Sodium hydroxide | for pH adjustment (pH: 7.5) |

TABLE 11-continued

| Components | (% by weight) Experiment 21 |
|---|---|
| Disodium edetate | 0.1 |
| Ethanol | 10.0 |
| Perfume | 0.2 |
| Purified water | balance |
| Total: | 100.0 |
| - Evaluation - | |
| Re-dispersibility: | A |
| Hair-color change: | A |

Notes of Table 11:
*14: FLAMENCO SATIN ORANGE 320 (rutile type, available from Mearl Co.); average particle diameter: 5.4 μm; proportion of particles with diameters of 20 μm or larger: 0.1% by volume or less.
*15: Silicone SH-3775M (available from Toray Dow Corning Corp.).

Experiment 22

Components as shown in Table 12 were mixed by a conventional method, and 45 g of the mixture thus obtained and about 1 g of stainless steel balls were put into a commercially available aerosol can (container), which was further filled with 5 g of an aerosol propellant (liquefied petroleum gas; 0.45 MPa). Thus, a hair cosmetic was obtained in the form that it was filled in a hair foam container. On the hair cosmetic thus obtained, the re-dispersibility and hair-color change were evaluated in the same manner as in Experiment 15.

Results obtained are shown in Table 12. As can be seen from Table 12, the hair cosmetic of Experiment 22 showed good results on both the re-dispersibility and the hair-color change. Moreover, it did not impart any unnaturally glittering impression to the hair.

TABLE 12

| Components | (% by weight) Experiment 22 |
|---|---|
| Titanium-dioxide-coated mica*16 | 3.0 |
| Carboxyvinyl polymer*10 | 0.03 |
| Amphoteric macromolecule*11 | 2.5 |
| Nonionic surfactant*12 | 0.5 |
| Anionic surfactant*13 | 0.3 |
| Glycerol | 0.3 |
| Isostearyl glyceryl ether | 0.2 |
| Sodium hydroxide | for pH adjustment (pH: 7.5) |
| Disodium edetate | 0.1 |
| Ethanol | 10.0 |
| Perfume | 0.2 |
| Purified water | balance |
| Total: | 100.0 |
| - Evaluation - | |
| Re-dispersibility: | A |
| Hair-color change: | A |

Notes of Table 12:
*16: FLAMENCO SATIN RED (rutile type, available from Mearl Co.); average particle diameter: 5.2 μm; proportion of particles with diameters of 20 μm or larger: 0.1% by volume or less.

Experiment 23

Components as shown in Table 13 were mixed by a conventional method, and 45 g of the mixture thus obtained and about 1 g of stainless steel balls were put into a commercially available aerosol container, which was further filled with 4 g of an aerosol propellant (liquefied petroleum gas; 0.45 MPa). Thus, a foam type hair cosmetic was obtained. On the foam type hair cosmetic thus obtained, the re-dispersibility and hair-color change were evaluated in the same manner as in Experiment 15.

Results obtained are shown in Table 13. As can be seen from Table 13, the hair cosmetic of Experiment 23 showed good results on both the re-dispersibility and the hair-color change. Moreover, it did not impart any unnaturally glittering impression to the hair.

TABLE 13

| Components | (% by weight) Experiment 23 |
|---|---|
| Titanium-dioxide-coated mica*17 | 4.0 |
| Carboxyvinyl polymer*10 | 0.1 |
| Amphoteric macromolecule*11 | 4.0 |
| Nonionic surfactant*12 | 0.5 |
| Olive oil | 0.1 |
| Ethanol | 10.0 |
| Perfume | 0.2 |
| Purified water | balance |
| Total: | 100.0 |
| - Evaluation - | |
| Re-dispersibility: | A |
| Hair-color change: | A |

Notes of Table 13:
*17: FLAMENCO SATIN BLUE (rutile type, available from Mearl Co.); average particle diameter: 5.2 μm; proportion of particles with diameters of 20 μm or larger: 0.1% by volume.

As described above, the hair cosmetics of Experiments 15 to 23 containing the titanium-dioxide-coated mica according to the present invention had a superior re-dispersibility, and also, when applied to hair, were able to well change the color of hair without imparting an unnaturally glittering impression.

What is claimed is:

1. A hair cosmetic comprising
   titanium-dioxide coated mica in an amount of 0.5% to 10% by weight, wherein said titanium-dioxide coated mica with particle diameters of 20 μm or larger is in a proportion of not more than 10% by volume of the total volume of the titanium-dioxide coated mica,
   a carboxyvinyl polymer in an amount of 0.01% to 0.2% by weight; and
   an amphoteric macromolecule having a molecular weight of 40,000 to 300,000 in an amount of 0.2% to 3% by weight.

2. The hair cosmetic according to claim 1, wherein the titanium-dioxide-coated mica with particle diameters of 20 μm or larger is in a proportion not more than 1% by volume in the total volume of the titanium-dioxide-coated mica.

3. The hair cosmetic of claim 1, wherein said titanium-dioxide coated mica with particle diameters of 20 μm or larger is in a proportion not more than 7% by volume in the total volume of the titanium-dioxide coated mica.

4. The hair cosmetic of claim 1, wherein said titanium-dioxide coated mica with particle diameters of 20 μm or larger is in a proportion not more than 5% by volume in the total volume of the titanium-dioxide coated mica.

5. The hair cosmetic of claim 1, wherein said titanium-dioxide coated mica with particle diameters of 20 μm or larger is in a proportion of 0.1% to 10% by volume in the total volume of the titanium-dioxide coated mica.

6. The hair cosmetic of claim 1, wherein the titanium-dioxide coated mica with particle diameters of 20 μm or larger is in a proportion of 0.1 to 7.3% in the total volume of titanium-dioxide-coated mica.

* * * * *